US00PP21719P2

(12) United States Plant Patent
Lyrene

(10) Patent No.: US PP21,719 P2
(45) Date of Patent: Feb. 22, 2011

(54) SOUTHERN HIGHBUSH BLUEBERRY PLANT NAMED 'FL02-40'

(50) Latin Name: *Vaccinium corymbosum L.*
Varietal Denomination: FL02-40

(75) Inventor: Paul M. Lyrene, Micanopy, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/587,283

(22) Filed: Oct. 5, 2009

(51) Int. Cl.
*A01H 5/00* (2006.01)

(52) U.S. Cl. ..... Plt./157
(58) Field of Classification Search ..... Plt./157

See application file for complete search history.

*Primary Examiner*—Susan B McCormick Ewoldt
(74) *Attorney, Agent, or Firm*—Jondle & Associates, P.C.

(57) ABSTRACT

A southern highbush blueberry (*Vaccinium corymbosum* L.) variety particularly distinguished by a very low chilling requirement (200 hours below 7° C.) with prolific early-spring leafing, a vigorous bush, a very early ripening (50% ripe berries in north Florida about April 21), and berries that are firm, sweet, and aromatic in flavor.

2 Drawing Sheets

STATEMENT REGARDING FEDERALLY SPONSORED RESEARCH

Figure 1:
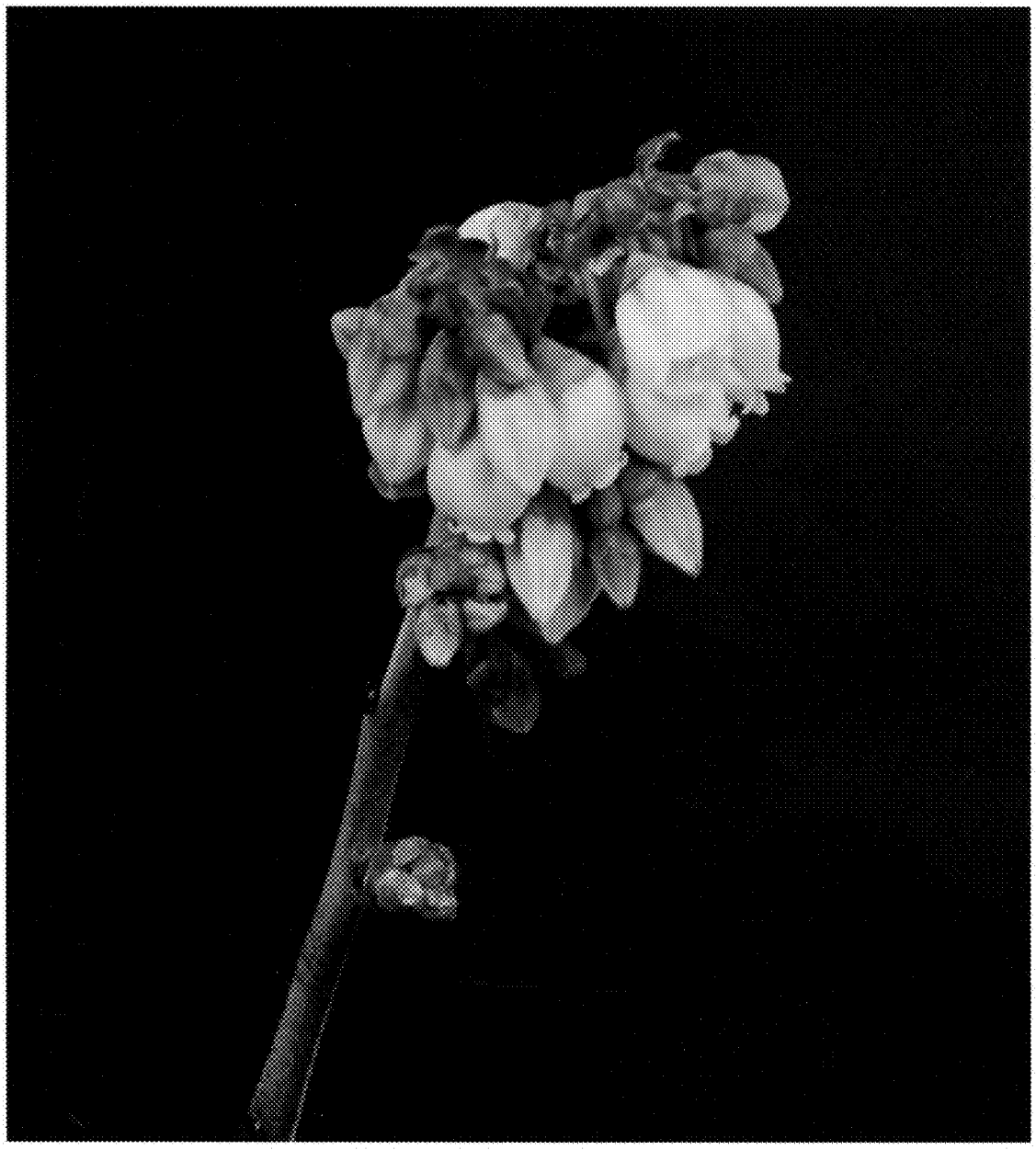

The present invention was supported in part by funds from the U.S. Government. The U.S. Government therefore may have certain rights in the invention.

Genus and species: *Vaccinium corymbosum* L.

Variety denomination: 'FL02-40'.

BACKGROUND OF THE NEW PLANT

The invention relates to a new and distinct variety of southern highbush blueberry (*Vaccinium corymbosum* L.) hybrid plant named 'FL02-40.' 'FL02-40' is a southern highbush blueberry clone distinguished by its very low chilling requirement, its prolific early-season leafing, and firm, sweet, aromatic berries that ripen during April when grown in north Florida. Several hundred plants of 'FL02-40' have been propagated by softwood cuttings at Gainesville, Fla., and the resulting plants have all been phenotypically indistinguishable from the original plant. Contrast is made to 'Star' (U.S. Plant Pat. No. 10,675), an important variety widely planted in Florida and Georgia for early-season blueberry production. The new variety is important because it has a lower chilling requirement than 'Star,' ripens earlier in the season, and has a sweeter, more aromatic berry.

'FL02-40' originated as a seedling from the cross 'FL95-54' (unpatented)×'FL97-125' (unpatented) made as part of the University of Florida breeding program in a greenhouse at Gainesville, Fla. in February 1999. The seedling was first fruited in a high-density field nursery in the spring of 2001. After the second year of fruiting in the field, in the spring of 2002, 'FL02-40' was propagated by softwood cuttings, and an experimental 15-plant test plot was established as part of a variety test at Windsor, Fla. in February 2003. Based on the early-season ripening and high berry quality of this plot, 'FL02-40' was repropagated by softwood cuttings in June 2005, and new test plots were planted the following winter at Windsor, Waldo, and Haines City, Fla. These plots, and the original plot, have been observed annually from flowering through fruit ripening each year, and no mutations or off-type plants have been observed.

SUMMARY OF THE INVENTION

The following are the most outstanding and distinguishing characteristics of this new cultivar when grown under normal horticultural practices in Florida.

1. A very low chilling requirement with prolific early-spring leafing;
2. A vigorous bush;
3. Very early ripening (50% ripe berries in north Florida about April 21); and
4. Berries that are firm, sweet, and aromatic in flavor.

DESCRIPTION OF THE PHOTOGRAPHS

The color chart used in this specification is "The Pantone Book of Color" (by Leatrice Eiseman and Lawrence Herbert; Harry N. Abrams, Inc., Publishers, New York, 1990). Where colors in the drawings differ from the Pantone color designations in the descriptions, the Pantone color designations are accurate. The colors shown are as true as can be reasonably obtained by conventional photographic procedures.

FIG. 1 shows several clusters of opening flowers during the early stages of flowering in early February. The flowers are pink before anthesis, especially in cold weather, but become white by anthesis. The relatively tight flower clusters are visible.

Figure 2:
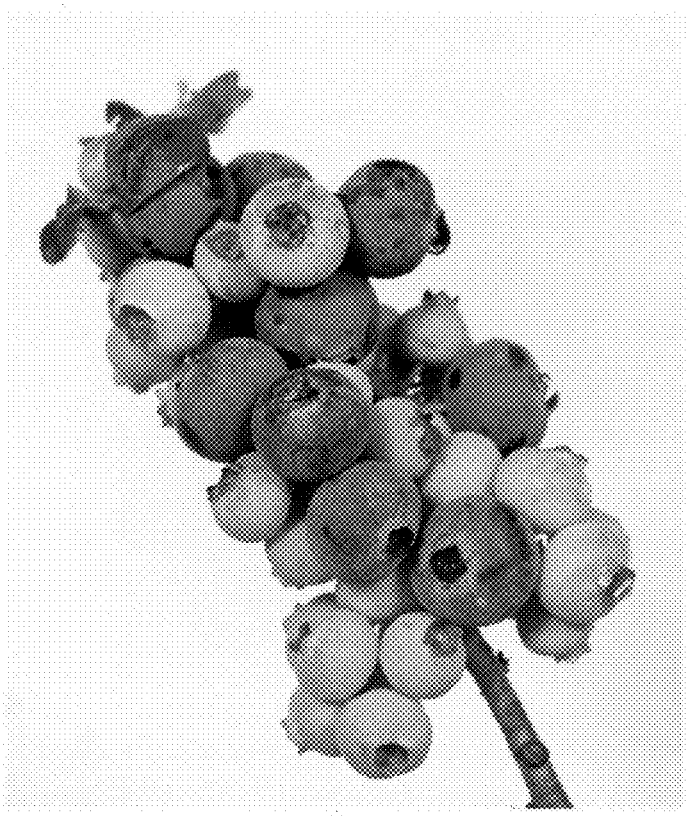

FIG. 2 shows several clusters of berries as they begin to ripen. The freckling pattern is due to naturally occurring minerals in the water being used in overhead irrigation of the plants and is not an inherent feature of the berries. Although not apparent in this figure, the berries within a cluster normally ripen within ten days of each other.

Figure 3:
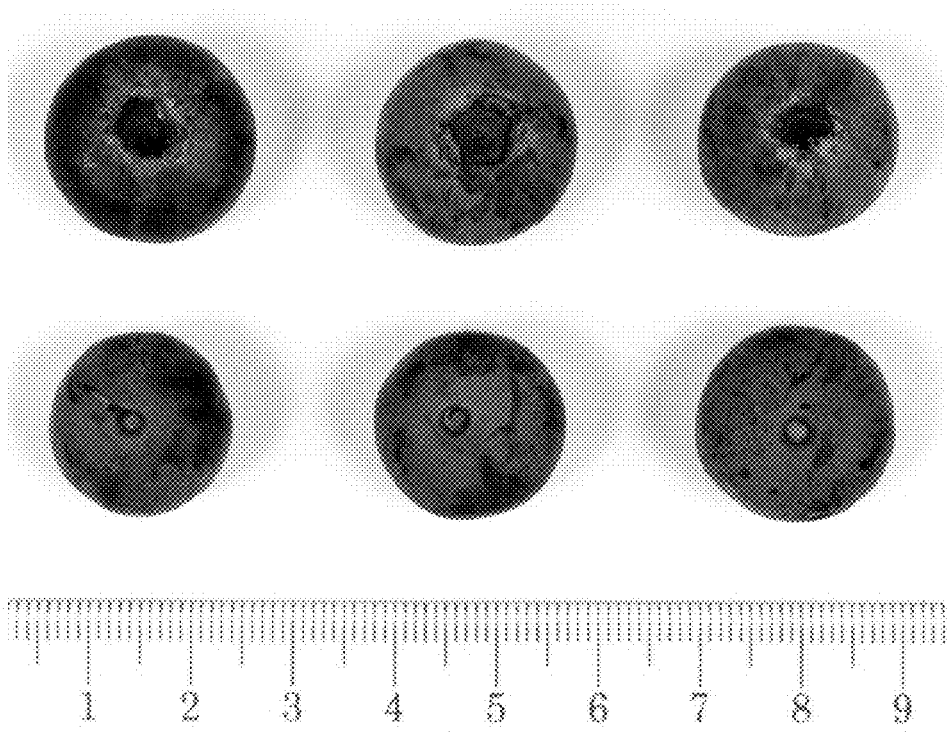

FIG. 3 shows berries at close range. The small, dry picking scars and the relatively undeveloped, amorphous calyx lobes are visible.

DESCRIPTION OF THE NEW CULTIVAR

The following detailed description sets forth the distinctive characteristics of 'FL02-40.' The data which define these characteristics were collected from asexual reproductions carried out in Florida. The plant history was taken on 3½-year-old plants. The following descriptions relate to plants grown in the field in north Florida (Windsor, Fla.). Color designations are from "The Pantone Book of Color" (by Leatrice Eiseman and Lawrence Herbert, Harry N. Abrams, Inc., Publishers, New York, 1990). Where the Pantone color designations differ from the colors in the drawings, the Pantone colors are accurate.

DETAILED BOTANICAL DESCRIPTION

Classification:

*Family.*—Ericaceae.

*Botanical.*—*Vaccinium corymbosum* L. var. 'FL02-40'.

*Common name.*—Southern Highbush Blueberry.

Parentage:

*Female parent.*—'FL 95-54,' a proprietary southern highbush blueberry plant (unpatented).

*Male parent.*—'FL97-125,' a proprietary southern highbush blueberry plant (unpatented).

*Market class.*—'FL02-40' produces southern highbush blueberries suitable for both the fresh and processed fruit markets.

Plant:

*General.*—Bush characteristics were taken from a plot of one-hundred 3½-year-old plants growing in a test plot in a commercial field near Windsor in northeast Florida.

*Plant height.*—1.3 m.

*Canopy* (*diameter measured at widest part of the bush*).—2.4 m.

*Plant vigor.*—High; more vigorous than 'Star'.

*Growth habit.*—Somewhat spreading, open growth habit.

*Flower bud density* (*number*) *along flowering twigs in January.*—Medium, about average for southern highbush blueberries.

*Twigginess.*—Low.

*Tendency toward evergreenness.*—Medium to high.

*Productivity.*—In northeast Florida, 'FL02-40' produces 4 to 6 pounds of berries per bush on plants 3 years old or older.

*Chilling requirement.*—200 hours below 7° C.

*Cold hardiness.*—Flowers and fruit are hardy to −3° C.; the plant is hardy to −15° C. during winter dormancy.

*Ease of propagation.*—'FL02-40' is easy to propagate from softwood cuttings; the plants survive and grow well in nursery beds.

Trunk and branches:

*Suckering tendency.*—Medium; 3½-year-old plants have an average of five major canes rising from a crown 30 cm in diameter.

*Surface texture* (*of strong, 6-month-old shoots observed in June*).—Smooth.

*Surface texture* (*of 3-year-old and older wood*).—Rough due to exfoliation and production of vertical cracks.

*Color of new twigs observed in June in the field.*—"Seafoam Green," Pantone 12-0313.

*Color of 3-year-old rough-textured canes.*—"Parchment," Pantone 13-0908.

*Internode length on strong, upright shoots measured in June.*—Average is 1.5 cm.

Leaves:

*Length, mean* (*including petiole, from tip of petiole to end of blade*).—5.4 cm.

*Width, mean* (*at widest point*).—2.9 cm.

*Shape.*—Ovate, terminating in a very short dew tip, 0.03 cm long, which is visible with a 15× microscope.

*Margin.*—Entire.

*Color.*—Upper surface: "Chive," Pantone 19-0323. Lower surface: "Piquant Green," Pantone 17-0235.

*Pubescence on upper surface of leaves.*—Very numerous white, short, curled hairs along the midrib. The petiole is also abundantly hirsute.

*Pubescence on the lower surface of leaves.*—Extremely numerous short, white, curled hairs along the midrib. Petiole also abundantly hirsute.

*Pubescence on margins.*—Numerous short, white hairs in places along the margin.

*Relative time of leafing versus flowering.*—In commercial fields in north Florida, where it is sprayed with hydrogen cyanamide in midwinter, 'FL02-40' begins to produce new leaves before the time of full bloom.

Flowers:

*Arrangement.*—Flowers are arranged alternately along a short, leafless, deciduous branch.

*Fragrance.*—Slight rose.

*Shape.*—Urceolate.

*Flowering period.*—Mean date of 50% open flowers in Windsor, Fla. is February 1; averages two weeks before 'Star'.

*Cluster* (*tight, medium, loose*).—Tight to medium.

*Average number of flowers per cluster.*—5.

*Pedicel.*—Length at time of anthesis: 0.4 cm. Color: "Red Violet," Pantone 17-1818 on the side exposed to direct sunlight.

*Peduncle.*—Length at time of anthesis: Highly variable; median is 0.5 cm. Color: "Red Violet," Pantone 17-1818 on the side exposed to direct sunlight.

*Calyx.*—Surface texture: Smooth. Color at anthesis: "Nile," Pantone 14-0223.

*Corolla.*—Diameter of tube (at widest point): 0.7 cm. Aperture diameter: 0.3 cm to 0.4 cm. Surface texture: Smooth. Color at anthesis: White. Length (from pedicel attachment point to corolla tip excluding the pedicel): Average of 1.0 cm.

Reproductive organs:

*Style length* (*top of ovary to stigma tip*).—0.8 cm.

*Location of tip of stigma relative to lip of the corolla.*—Stigma tip extends 0.1 cm beyond the edge of the corolla tube.

*Pollen.*—Abundance of shed: High. Staining with 2% acetocarmine (a measure of potential pollen fertility): Approximately 98% of the tetrads appear normal and well-formed and stain normally. Color of dried pollen: "Winter White," Pantone 11-0507.

*Self fruitfulness.*—Low to medium. Planting in field configurations that promote cross pollination with other southern highbush clones is recommended for all southern highbush blueberry plants in Florida.

Fruit:

*Mean date of first commercial harvest* (*25% of berries ripe*).—April 5.

*Mean date of mid-harvest in northeast Florida.*—April 21 compared to April 25 for 'Star'.

*Mean date of last harvest.*—May 1.

*Diameter of calyx aperture on mature berry.*—0.5 cm. The calyx aperture is unusually deep, with a 0.2 cm to 0.3 cm depression from the berry surface to the point where the pistil is attached to the ovary.

*Size and shape of calyx lobes on mature berry.*—Small and irregular, not making a well-defined five-pointed star.

*Pedicel length on ripe berry.*—Median is 0.5 cm.

*Peduncle length on ripe berry.*—Variable, median is 0.5 cm.

*Detachment force for ripe berries.*—Very low.

*Number of berries per cluster.*—Median is 6.

Berry:

*Cluster* (*tight, medium, or loose*).—Medium.

*Weight* (*on well-pruned plants*).—2.3 g per berry compared to 2.0 g per berry for 'Star'.

*Height.*—1.5 cm.

*Width.*—1.7 cm.

*Shape.*—Subglobose; slightly flattened from top to bottom.

*Surface color of immature berries, with bloom.*—"Frozen Dew," Pantone 13-0513.

*Surface color of mature berries while on the plant.*—"Thistle," Pantone 14-3907.

*Surface color of ripe berry after polishing.*—Shiny black.

*Surface wax.*—Medium in amount and in persistence during handling of the berry.

*Pedicel scar.*—Small and dry.

*Firmness.*—High.

*Flavor.*—Excellent; sweet, subacid, and with aromatic overtones.

*Texture.*—Good; small seeds and thin skinned.

Seeds:

*Color of dried seeds.*—"Bran," Pantone 17-1336.

*Weight of well-developed dried seed.*—0.6 mg per seed.

*Length of well-developed dried seed* (*mean*).—0.2 cm.

Resistance to diseases, insects, and mites: 'FL02-40' is highly vigorous, but has shown only medium survival in the field in northeast Florida. Because it flowers and leafs very early, it is subject to damage during late freezes. 'FL02-40' should be planted on well-drained soil and is best adapted in areas where January and February freezes are less severe than in Gainesville. 'FL02-40' is expected to grow well in blueberry growing areas with low summer rainfall. The reaction of 'FL02-40' to the fungal species that cause summer leaf spots is typical of other southern highbush cultivars, and fungicide applications may be needed after harvest to reduce foliar diseases.

COMPARISON WITH PARENTAL AND KNOWN CULTIVARS

'FL02-40' differs from the proprietary female (seed) parent 'FL95-54' (unpatented) in that 'FL02-40' has a larger berry, more prolific early-spring leafing, and a somewhat more spreading growth habit than 'FL95-54.'

'FL02-40' differs from the male (pollen) parent 'FL97-125' (unpatented) in that 'FL02-40' has a more vigorous bush, larger leaves, a larger berry, and a sweeter, more aromatic flavor than 'FL95-54.'

'FL02-40' differs from the commercial variety 'Star' (U.S. Plant Pat. No. 10,675), an important variety widely planted in Florida and Georgia for early-season blueberry production, in that 'FL02-40' has a lower chilling requirement, ripens earlier in the season, and has a sweeter, more aromatic berry than 'Star.'

I claim:

1. A new and distinct variety of southern highbush blueberry plant as shown and described herein.

* * * * *